United States Patent
Gibson et al.

(10) Patent No.: US 9,322,764 B2
(45) Date of Patent: Apr. 26, 2016

(54) ADSORPTION MATERIAL-BASED HUMIDITY SENSOR

(71) Applicant: Xerox Corporation, Norwalk, CT (US)

(72) Inventors: George A. Gibson, Fairport, NY (US); Linn C. Hoover, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 351 days.

(21) Appl. No.: 13/913,567

(22) Filed: Jun. 10, 2013

(65) Prior Publication Data

US 2014/0360253 A1    Dec. 11, 2014

(51) Int. Cl.
   *G01N 19/10*    (2006.01)
(52) U.S. Cl.
   CPC ..................... *G01N 19/10* (2013.01)
(58) Field of Classification Search
   CPC ............................. G01N 19/10; H01H 37/02
   USPC ............ 73/73, 335.13, 29.01–29.02, 335.11; 338/34–35; 340/602–603; 200/61.06
   See application file for complete search history.

(56) References Cited

U.S. PATENT DOCUMENTS

| | | | |
|---|---|---|---|
| 2,267,164 A * | 12/1941 | Newton | 337/300 |
| 3,936,793 A * | 2/1976 | Armstrong | 337/300 |
| 4,489,603 A * | 12/1984 | Fukami et al. | 73/335.11 |
| 4,854,160 A | 8/1989 | Glatt | |
| 5,028,906 A | 7/1991 | Moriya et al. | |
| 6,032,004 A | 2/2000 | Mirabella, Jr. et al. | |
| 6,043,096 A | 3/2000 | Evtodienko et al. | |
| 6,268,094 B1 | 7/2001 | Allen et al. | |
| 6,654,573 B2 | 11/2003 | Carlson et al. | |
| 6,698,378 B1 | 3/2004 | Dick et al. | |
| 7,451,643 B2 | 11/2008 | Singh et al. | |
| 2004/0243270 A1 | 12/2004 | Amirthalingam | |
| 2005/0078557 A1 | 4/2005 | Andersen | |
| 2009/0045039 A1 * | 2/2009 | Hayashi et al. | 200/238 |

* cited by examiner

*Primary Examiner* — Peter Macchiarolo
*Assistant Examiner* — Anthony W Megna Fuentes
(74) *Attorney, Agent, or Firm* — Gibb & Riley, LLC

(57) ABSTRACT

Apparatuses include a base, a linear beam of paper material connected to the base, and an adhesive surface connected to the base adjacent the linear beam. In its un-deformed state, the linear beam is straight and elongated. A coating (e.g., a flexible moisture barrier) covers only a second side along the length of the linear beam (and does not cover a first side). The adhesive surface is a contact self-adhesive. The linear beam develops a curvature toward the adhesive surface from exposure to an atmospheric excessive moisture level above a previously established moisture level. A sufficient amount of curvature causes the linear beam to contact the adhesive surface, and the linear beam remains permanently attached to the adhesive surface after contacting the adhesive surface, thereby indicating that at some point the previously established moisture level has been exceeded.

16 Claims, 4 Drawing Sheets

ADSORPTION MATERIAL-BASED HUMIDITY SENSOR

BACKGROUND

Systems and methods herein generally relate to moisture sensors, and more particularly to moisture sensors that change shape based on different levels of moisture.

Many packaged goods are sensitive to the presence of humidity, and such goods may be prone to degradation or spoilage in the presence of excess humidity. Frequently packages of silica gel are included in packaging in hope that excessive moisture can be absorbed. Such packets are generally small and do not contain indicating means, therefore do not provide an easy way to tell if the humidity was higher than that considered allowable.

A conventional hygrometer measures relative humidity levels, and often includes a pointer moving over a dial. Some conventional micrometers connect the pointer to a coil made from multiple materials that have different expansion/contraction rates based on different humidity levels, which causes the coil to curl and uncurl with different moisture levels, thereby moving the pointer on the hygrometer according to the moisture level.

Additional devices can change electrical conductivity based on different levels of humidity (where the electrical connective nature of water changes the measured electrical resistance) or can change color when excessive amounts of humidity are encountered (based upon chemical reactions). However, all such devices require complex metalworking, chemical composition, electrical structures, etc., which drives the price of such devices to the point that they cannot economically be used in all situations where the moisture/humidity needs to be monitored.

SUMMARY

A general exemplary apparatus herein includes a linear beam of fibrous material and an adhesive surface adjacent the linear beam. In its un-deformed state, the linear beam is straight and elongated and, therefore, has a length greater than a width. Further, the linear beam has a first side and an opposing second side along the length of the linear beam. A coating (e.g., a flexible moisture barrier) covers only the first side along the length of the linear beam (and does not cover the second side). The adhesive surface is a contact self-adhesive.

The fibrous material changes length upon adsorption of moisture, and the linear beam develops a curvature toward the adhesive surface from exposure to an excessive moisture level above a previously established moisture level. The curvature is caused by the moisture changing the length of the first side of the linear beam, without changing the second side of the linear beam (which is protected from the moisture by the coating). More specifically, the coating decreases the amount of the moisture entering the second side relative to the first side, and more of the moisture entering the first side relative to the second side causes the first side to change more in length relative to the second side, thereby causing the previously straight linear beam to curve.

A sufficient amount of curvature causes the linear beam to curve a distance sufficient to contact the adhesive surface. Because of the self-adhesive nature of the adhesive surface, the linear beam remains permanently attached to the adhesive surface after contacting the adhesive surface, thereby indicating that at some point the previously established moisture level has been exceeded.

Alternative devices include a detector circuit for detecting and reporting excessive moisture levels. In these devices, at least the first side of the linear beam and the adhesive surface comprise electrical conductors (and the first side of the linear beam and the adhesive surface form portions of the detector circuit). When the first side of the linear beam contacts the adhesive surface, it forms an electrical connection completing the detector circuit and indicating an excessive moisture level above the previously established moisture level.

A more specific exemplary apparatus herein includes a base, a linear beam of paper material connected to the base, and an adhesive surface connected to the base adjacent the linear beam. In its un-deformed state, the linear beam is straight and elongated and, therefore, has a length greater than a width. Further, the linear beam has a first side and an opposing second side along the length of the linear beam. A coating (e.g., a flexible humidity barrier) covers only the first side along the length of the linear beam (and does not cover the second side). The adhesive surface is a contact self-adhesive.

The paper material changes in length upon adsorption of atmospheric humidity, and the linear beam develops a curvature toward the adhesive surface from exposure to an atmospheric excessive humidity level above a previously established humidity level. The curvature is caused by the atmospheric humidity changing the length of the first side of the linear beam a greater amount than the second side of the linear beam (which is protected from the atmospheric humidity by the coating). More specifically, the coating decreases the amount of the atmospheric humidity entering the second side relative to the first side, and more of the atmospheric humidity entering the first side relative to the second side causes the first side to change in length a greater amount relative to the second side, thereby causing the previously straight linear beam to curve.

A sufficient amount of curvature causes the linear beam to curve a distance sufficient to contact the adhesive surface. Because of the self-adhesive nature of the adhesive surface, the linear beam remains permanently attached to the adhesive surface after contacting the adhesive surface, thereby indicating that at some point the previously established humidity level has been exceeded.

Alternative devices include a detector circuit for detecting and reporting excessive humidity levels. In these devices, at least the first side of the linear beam and the adhesive surface comprise electrical conductors (and the first side of the linear beam and the adhesive surface form portions of the detector circuit). When the first side of the linear beam contacts the adhesive surface, it forms an electrical connection completing the detector circuit and indicating an excessive humidity level above the previously established humidity level.

These and other features are described in, or are apparent from, the following detailed description.

BRIEF DESCRIPTION OF THE DRAWINGS

Various exemplary systems and methods are described in detail below, with reference to the attached drawing figures, in which.

DETAILED DESCRIPTION

As mentioned above, conventional humidity detection devices can require complex metalworking, chemical compositions, electrical structures, etc., which drives the price of such devices to the point that they cannot economically be used in all situations where the moisture/humidity needs to be monitored. In view of these issues, the devices herein utilize a low-cost strip or beam of fibrous material (such as paper) that is moisture protected on one side. Upon exposure to excessive moisture conditions, the low-cost beam curls and attaches to an adhesive contact (and/or forms an electrical connection) thereby permanently recording the excessive moisture condition. Because devices herein utilize a low-cost beam of fibrous material and a simple adhesive contact, they are extremely inexpensive and their use can be economically justified in situations where conventional humidity detection devices would not be economically justified. This allows more devices to be protected from excessive moisture conditions than would be protected conventionally, which decreases use of potentially defective (corroded or spoiled) components, thereby increasing yield and reducing waste.

FIGS. 1-5 illustrate exemplary apparatuses herein. Such apparatuses includes a base 104, a linear beam 100 of fibrous material (such as paper) connected to the base 104, and an adhesive surface 106 connected to the base 104 adjacent the linear beam 100. The base 104 and adhesive surface 106 can be made of any material with sufficient strength to support the elements shown and, therefore, can be made of cardboard, plastic, glass, wood, metal, etc. The adhesive surface 106 can comprise any contact adhesive such as glues, magnets, hook and loop fasteners, or any other substance that has the ability to permanently make a connection with the linear beam 100.

Figure 1:
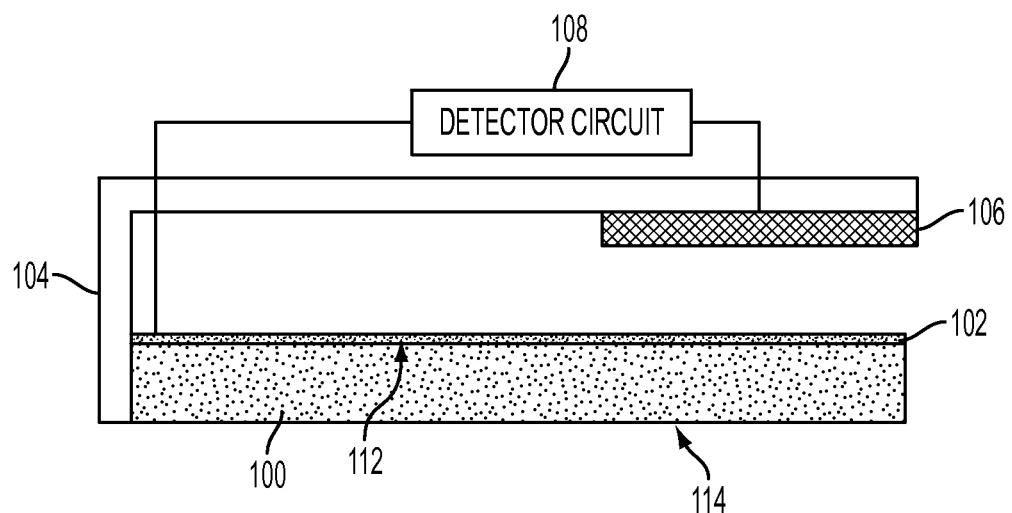
FIG. 1 is a schematic diagram of a un-deformed device herein.

The shape of the linear beam 100 can be any straight elongated shape, such as and elongated rectangle, an elongated triangular shape, an elongated oval shape, a plank shape, and I-beam shape, a box beam shape, etc. As shown in FIG. 1, in its un-deformed state, the linear beam 100 is straight and elongated and, therefore, the beam's length is greater than its width. For example, the length (shown horizontally in FIG. 1) can be 5×, 10×, 25× the width (shown vertically in FIG. 1 (and the width can also be in the direction coming out of the page in FIG. 1). Thus, stated simplistically, the length of the linear beam 100 is perpendicular to its width. Further, the linear beam 100 has a first side 112 and an opposing second side 114 along the length of the linear beam 100. As shown in the drawings, the first side 112 is the top of the linear beam 100 and the second side 114 is the bottom of the linear beam 100.

A coating 102 (e.g., a flexible humidity barrier) covers only the first side 112 along the length of the linear beam 100 (and does not cover the first side 112). The coating 102 can comprise any moisture resistant material such as wax, rubber, varnish, plastic, etc., and can be applied to the linear beam 100 by spraying, dipping, printing, gluing, gravure of offset coating, mechanical attachment, etc.

Further, the materials chosen for the linear beam 100 and the coating 102 are dependent upon the environment in which the moisture detection devices will be utilized. In some cases, the moisture that is detected is water vapor (humidity); and, therefore, the linear beam 100 can be easily formed from paper (because paper readily curls in the presence of humidity) and the coating 102 can be any water-resistant or water-proof material. To the contrary, if the moisture to be detected is vapors of other gases that may precipitate the material for the linear beam 100 comprises a fibrous material that chemically reacts with the vapor such that it shrinks (or expands) in the presence of a liquid precipitate form of such a vapor. Expanded polymeric films, for instance, can be shown to shrink in the presence of the vapors of materials that are solvents for the polymer. Virtually any materials could be used for the linear beam 100 and the coating 102 as such materials are dependent upon the specific environment in which the devices will be utilized.

The length of the material of the linear beam 100 changes upon adsorption of atmospheric precipitated liquids (such as water), and the linear beam 100 develops a curvature toward the adhesive surface 106 from exposure to an atmospheric excessive moisture level above a previously established humidity level. The curvature is caused by the atmospheric moisture changing the length of the first side 112 of the linear beam 100, without changing the length of the second side 114 of the linear beam 100 (which is protected from the atmospheric moisture by the coating 102). More specifically, the coating 102 decreases the amount of the atmospheric moisture entering the second side 114 relative to the first side 112, and more of the atmospheric moisture entering the first side 112 relative to the second side 114 causes the first side 112 to change in length relative to the second side 114, thereby causing the previously straight linear beam 100 to curve.

Depending upon the specific gaseous environment and the makeup of the linear beam 100, the length of the linear beam may increase or decrease. In the example shown in FIGS. 1-5, the first side 112 decreases in length causing the beam 102 curve upward toward the adhesive surface 106. However, if exposure to the moisture causes the first side 112 to increase in length, either the location of the adhesive surface 106 could be reversed or the linear beam 100 could be flipped so that the relatively expanding length side of the beam causes the beam to curve toward the adhesive surface 106.

Figure 2:
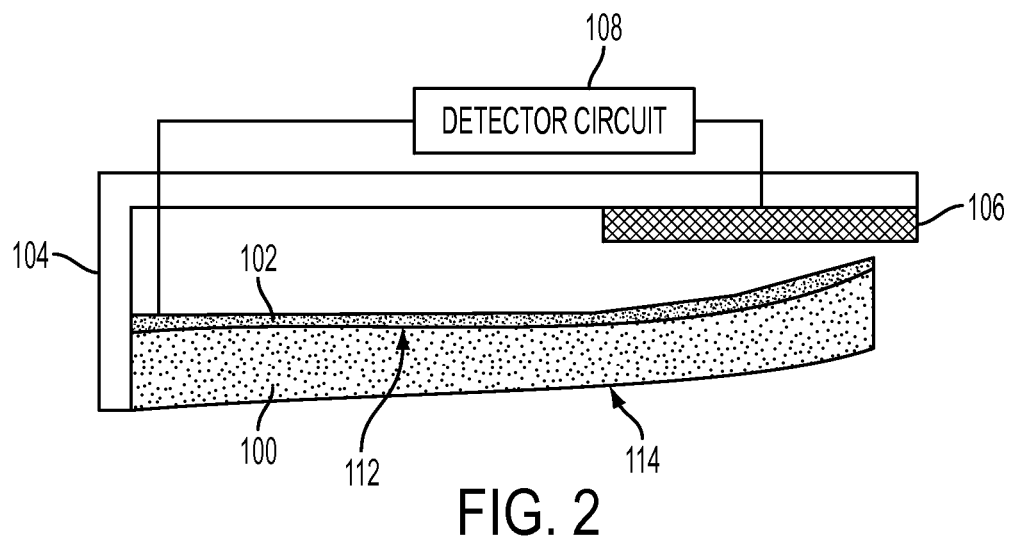
FIG. 2 is a schematic diagram of a partially deformed device herein.
Figure 3:
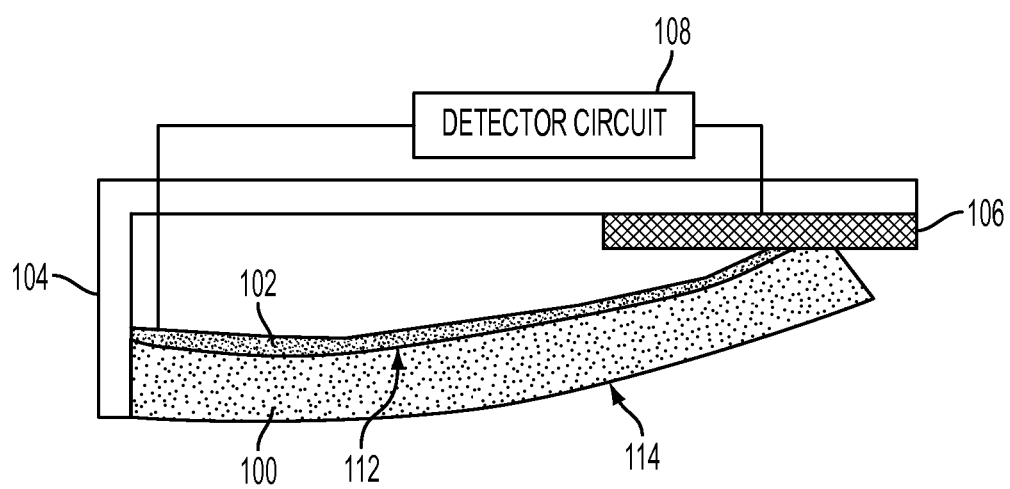
FIG. 3 is a schematic diagram of a permanently deformed device herein.
Figure 4:
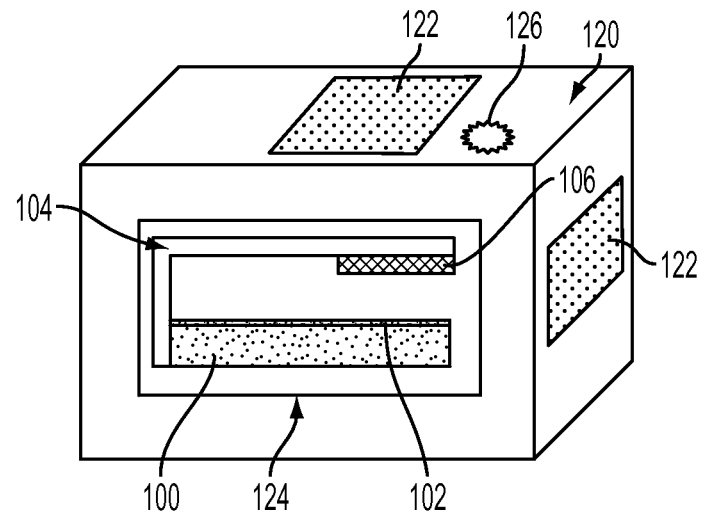
FIG. 4 is a schematic diagram of a un-deformed device herein.

FIG. 1 illustrates the linear beam 100 when it is in an un-deformed straight shape, FIG. 2 illustrates the linear beam 100 when it is in a partially deformed shape, and FIG. 3 illustrates the linear beam 100 when it is in a deformed shape sufficiently curved to contact the adhesive surface 106. The moisture detection device shown in FIGS. 1-3 can also be included within a container 120 shown in FIGS. 4 and 5. The container 120 can include openings or filters 122 that allow atmospheric conditions to reach the moisture detection device. Further, the container 120 can include a transparent window 124 to allow the moisture detection device to be observed from outside the container 120.

A sufficient amount of curvature causes the linear beam 100 to curve a distance sufficient to contact the adhesive surface 106. Therefore, the initial moisture content of the linear beam 100 when it is in an un-deformed straight shape can be established during manufacture so as to control the atmospheric moisture level required to cause the linear beam 100 to curve enough to contact the adhesive surface 106. Similarly, the distance between the linear beam 100 when it is in an un-deformed straight shape and the adhesive surface 106 can be designed to control the atmospheric moisture level required to cause the linear beam 100 to curve enough to contact the adhesive surface 106. Therefore, by controlling the moisture content of the straight linear beam 100 and the distance between the straight linear beam and the adhesive surface 106, the moisture detection devices herein can be customized to monitor for different excessive moisture levels (and provide a visual indication of the same).

Because of the self-adhesive nature of the adhesive surface 106, the linear beam 100 remains permanently attached to the adhesive surface 106 after contacting the adhesive surface 106, thereby indicating that at some point the previously established moisture level has been exceeded. Thus, while the moisture level might vary before the moisture detection devices shown in FIGS. 1-5 are observed by the user, because the linear beam 100 becomes permanently attached to these adhesive surface 106, the user can be made aware (through this shape change visual indication) that at some point the moisture level exceeded one of many different preset levels which the moisture detection device was designed to identify.

Alternative devices include a detector circuit 108 for detecting and reporting excessive humidity levels. In these devices, at least the first side 112 of the linear beam 100 (potentially by way of a conductive coating 102) and the adhesive surface 106 comprise electrical conductors (and the first side 112 of the linear beam 100 and the adhesive surface 106 form portions of the detector circuit 108). For example, the linear beam 100 and adhesive surface 106 can be made of conductive materials, or can have conductive materials embedded therein. When the first side 112 of the linear beam 100 contacts the adhesive surface 106 (or possibly when the coating 102 contacts the adhesive surface 106), it forms an electrical connection completing the detector circuit 108, which indicates an excessive humidity level above the previously established humidity level.

Figure 5:
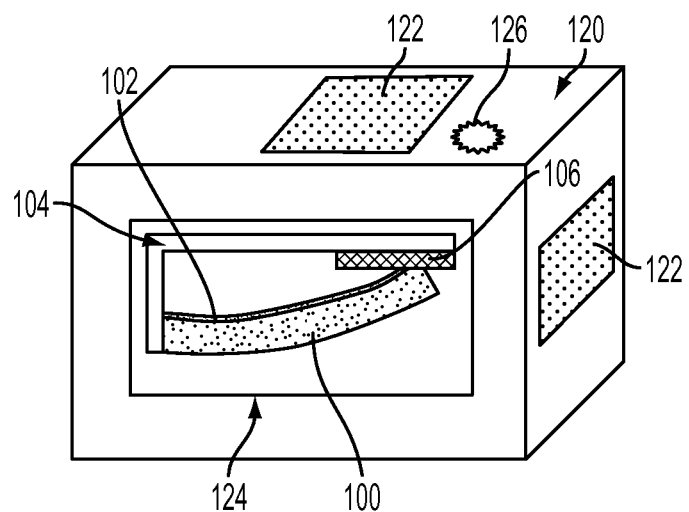
FIG. 5 is a schematic diagram of a permanently deformed device herein.

The signal that is produced by the protector circuit 108 can be stored or output to another device. Additionally, the container 120 can include a visual indicator 126 (such as a light, etc., or item 126 can illustrate a wireless communication device such as an antenna) that can light up or change its electronic or visual appearance (as shown in FIG. 5) when the linear beam 100 makes contact with the adhesive surface 106.

Thus, as shown above, in some examples, the moisture detection device is a very low-cost paper based device that can easily be fabricated into packages and that allows real time assessment of internal humidity or humidity history. The sensor can use paper that is dried by heat and vacuum and coated on one side. A beam of such paper will curl toward the coated surface as water is absorbed into the uncoated side. The exact rate at which this occurs and the extent of the deflection depends on the paper type, the coating type and the thickness of both. Several methods can be used to exploit this property of the coated paper composite. In the simplest case the mechanism described above can be visible through a transparent window in the package where, within the package a cavity has been created that allows the curvature to develop.

More sophisticated devices use a conductive top layer that completes a circuit when the curvature has developed. This is, then, a switch is closed when the environment is humid. As such the device could be employed in a radio frequency identification (RFID) or near field communication (NFC) pollable device (represented by item 126 in FIGS. 4 and 5) indicating the state of the contents of a box or other similar container without opening it. The device can operate in a reversible manner with the contact opening and closing as the moisture content in the container changes. The application of the pressure sensitive adhesive pad, such as a glue dot renders the mechanism irreversible changing the sensor from a "current state" reporter to a historical threshold indicator.

Figure 6:
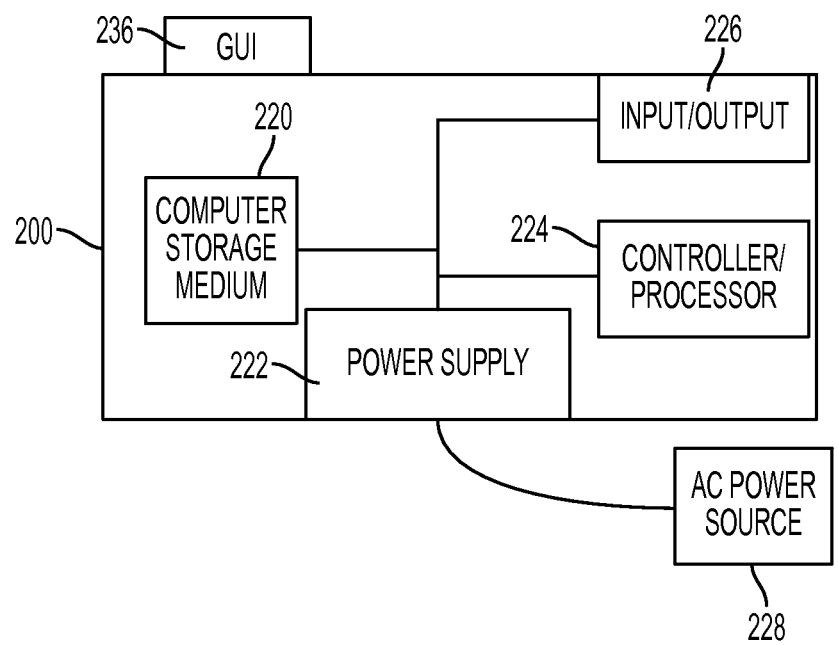
FIG. 6 is a schematic diagram illustrating devices herein.

FIG. 6 illustrates a computerized device 200, which can be used with systems and methods herein (such as the detector circuit 108) and can comprise, for example, a server, a personal computer, a portable computing device, etc. The computerized device 200 includes a controller/processor 224 and a communications port (input/output) 226 operatively connected to the processor 224 and to the computerized network external to the computerized device 200. Also, the computerized device 200 can include at least one accessory functional component, such as a graphic user interface assembly 236 that also operate on the power supplied from the external power source 228 (through the power supply 222).

The input/output device 226 is used for communications to and from the computerized device 200. The processor 224 controls the various actions of the computerized device. A non-transitory computer storage medium device 220 (which can be optical, magnetic, capacitor based, etc.) is readable by the processor 224 and stores instructions that the processor 224 executes to allow the computerized device to perform its various functions, such as those described herein. Thus, as shown in FIG. 6, a body housing 200 has one or more functional components that operate on power supplied from the alternating current (AC) 228 by the power supply 222. The power supply 222 can comprise a power storage element (e.g., a battery) and connects to an external alternating current power source 228 and converts the external power into the type of power needed by the various components.

Various electronic devices discussed above can include chip-based central processing units (CPU's), input/output devices (including graphic user interfaces (GUI), memories, comparators, processors, etc. are well-known and readily available devices produced by manufacturers such as Dell Computers, Round Rock Tex., USA and Apple Computer Co., Cupertino Calif., USA. Such computerized devices commonly include input/output devices, power supplies, processors, electronic storage memories, wiring, etc., the details of which are omitted herefrom to allow the reader to focus on the salient aspects of the systems and methods described herein.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements). Further, the terms automated or automatically mean that once a process is started (by a machine or a user), one or more machines perform the process without further input from any user.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Unless specifically defined in a specific claim itself, steps or components of the systems and methods herein cannot be implied or imported from any above example as limitations to any particular order, number, position, size, shape, angle, color, or material.

What is claimed is:

1. An apparatus comprising:
   a linear beam of material having a length greater than a width, and having a first side and a second side along said length of said linear beam, said first side being opposite said second side;
   a coating covering only one of said first side and said second side along said length of said linear beam; and
   an adhesive surface positioned a distance from said linear beam, said linear beam developing a curvature from exposure to an excessive moisture level above a previously established moisture level, said first side changing in length a greater amount relative to said second side upon more moisture entering said first side relative to said second side, said curvature causing said first side of said linear beam to contact said adhesive surface, and said linear beam remaining attached to said adhesive surface after contacting said adhesive surface.

2. The apparatus according to claim 1, said material decreasing in length upon adsorption of moisture.

3. The apparatus according to claim 1, said coating comprising a flexible moisture barrier.

4. The apparatus according to claim 1, further comprising a detector circuit, said first side of said linear beam comprising an electrical conductor, said adhesive surface comprising an electrical conductor, said first side of said linear beam and said adhesive surface comprising portions of said detector circuit, said first side of said linear beam contacting said adhesive surface forming an electrical connection completing said detector circuit, and said detector circuit indicating said excessive moisture level above said previously established moisture level based on said electrical connection completing said detector circuit.

5. An apparatus comprising:

a linear beam of paper material having a length greater than a width, and having a first side and a second side along said length of said linear beam, said first side being opposite said second side;

a coating covering said first side along said length of said linear beam; and an adhesive surface positioned a distance from said linear beam, said linear beam developing a curvature from exposure to an excessive moisture level above a previously established moisture level, said first side changing in length a greater amount relative to said second side upon more moisture entering said first side relative to said second side, said curvature causing said first side of said linear beam to contact said adhesive surface, and said linear beam remaining attached to said adhesive surface after contacting said adhesive surface.

6. The apparatus according to claim 5, said paper material decreasing in length upon adsorption of moisture.

7. The apparatus according to claim 5, said coating comprising a flexible moisture barrier.

8. The apparatus according to claim 5, further comprising a detector circuit, said first side of said linear beam comprising an electrical conductor, said adhesive surface comprising an electrical conductor, said first side of said linear beam and said adhesive surface comprising portions of said detector circuit, said first side of said linear beam contacting said adhesive surface forming an electrical connection completing said detector circuit, and said detector circuit indicating said excessive moisture level above said previously established moisture level based on said electrical connection completing said detector circuit.

9. An apparatus comprising:

a linear beam of paper material having a length greater than a width, and having a first side and a second side along said length of said linear beam, said first side being opposite said second side;

a coating covering said first side along said length of said linear beam; and an adhesive surface comprising a contact adhesive positioned a distance from said linear beam, said linear beam developing a curvature toward said adhesive surface from exposure to atmospheric moisture above a previously established moisture level, said first side changing in length a greater amount relative to said second side upon more moisture entering said first side relative to said second side, said curvature causing said first side of said linear beam to contact said adhesive surface, and said linear beam permanently remaining attached to said adhesive surface after contacting said adhesive surface.

10. The apparatus according to claim 9, said paper material decreasing in length upon adsorption of said atmospheric moisture.

11. The apparatus according to claim 9, said coating comprising a flexible moisture barrier.

12. The apparatus according to claim 9, further comprising a detector circuit, said first side of said linear beam comprising an electrical conductor, said adhesive surface comprising an electrical conductor, said first side of said linear beam and said adhesive surface comprising portions of said detector circuit, said first side of said linear beam contacting said adhesive surface forming an electrical connection completing said detector circuit, and said detector circuit indicating said atmospheric moisture above said previously established moisture level based on said electrical connection completing said detector circuit.

13. An apparatus comprising:

a base;

a linear beam of paper material connected to said base, said linear beam having a length greater than a width, and having a first side and a second side along said length of said linear beam, said first side being opposite said second side;

a coating covering only said first side along said length of said linear beam and not covering said second side; and an adhesive surface connected to said base positioned a distance from said linear beam, said adhesive surface comprising a contact self-adhesive, said linear beam developing a curvature toward said adhesive surface from exposure to an excessive humidity level above a previously established humidity level, said first side changing in length a greater amount relative to said second side upon more moisture entering said first side relative to said second side, a sufficient amount of said curvature causing said first side of said linear beam to contact said adhesive surface, and said linear beam remaining permanently attached to said adhesive surface after contacting said adhesive surface.

14. The apparatus according to claim 13, said paper material decreasing in length upon adsorption of atmospheric humidity.

15. The apparatus according to claim 13, said coating comprising a flexible humidity barrier.

16. The apparatus according to claim 13, further comprising a detector circuit,
- said first side of said linear beam comprising an electrical conductor,
- said adhesive surface comprising an electrical conductor,
- said first side of said linear beam and said adhesive surface comprising portions of said detector circuit,
- said first side of said linear beam contacting said adhesive surface forming an electrical connection completing said detector circuit, and
- said detector circuit indicating said excessive humidity level above said previously established humidity level based on said electrical connection completing said detector circuit.

* * * * *